Figure 1:
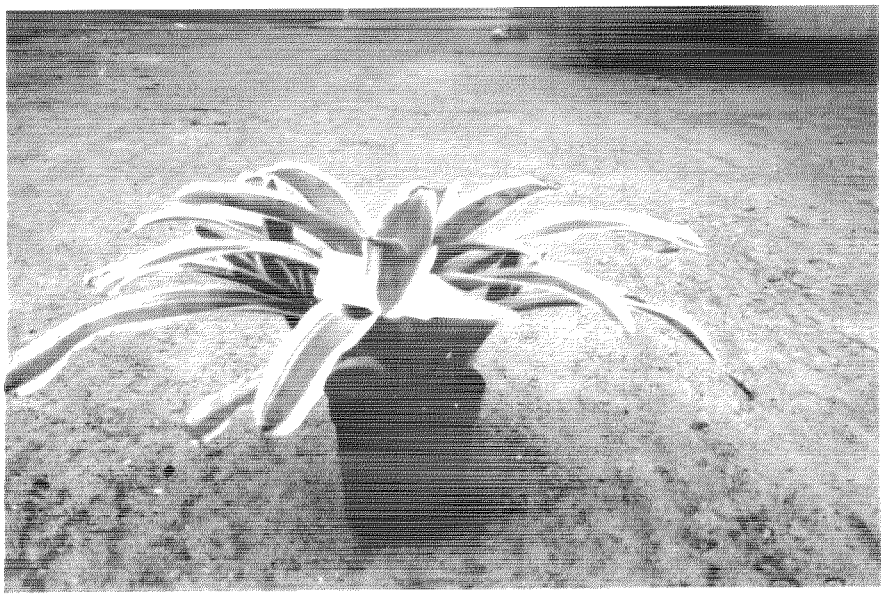

US00PP10718P

United States Patent [19]

Skotak, Jr.

[11] Patent Number: Plant 10,718

[45] Date of Patent: Dec. 8, 1998

[54] NEOREGELIA PLANT NAMED 'ANNICK'

[76] Inventor: Chester Skotak, Jr., Apt. 652, Alajuela, Costa Rica

[21] Appl. No.: 893,784

[22] Filed: Jul. 11, 1997

[51] Int. Cl.[6] ..... A01H 5/00

[52] U.S. Cl. ..... Plt./88.8

[58] Field of Search ..... Plt./88.8

[56] References Cited

U.S. PATENT DOCUMENTS

P.P. 9,598 7/1996 Skotak, Jr. ..... Plt./88.8

P.P. 9,599 7/1996 Skotak, Jr. ..... Plt./88.8

*Primary Examiner*—Howard J. Locker

*Assistant Examiner*—Kent L. Bell

*Attorney, Agent, or Firm*—Foley & Lardner

[57] ABSTRACT

A new and distinct cultivar of neoregelia plant named 'Annick', characterized by its leaves with a greyed-yellow margin (R.H.S. 160B) and dark green center (R.H.S. 147 A–B); the innermost leaves at the center of the rosette, when in flower, are overlayed with red-purple (R.H.S. 59 A–60A); the innermost leaves at the center of the rosette hold their red-purple color for 3 to 5 months during and after flowering; and the plant produces large numbers of offsets.

2 Drawing Sheets

The present invention comprises a new and distinctive cultivar of Neoregelia hybrid, botanically known as Neoregelia and hereinafter referred to by the name 'Annick'.

Neoregelia species are tank epiphytes with stemless inflorescences and flowers that barely rise above the water in the center of the plants. 'Annick' can be advantageously grown as a single pot plant in order to display its symmetrically rosette plant form.

The new cultivar is a product of a planned breeding program, and was originated from a cross made by the inventor Chester Skotak, Jr. during such program in Balsa, Costa Rica in 1988. The female or seed parent was an unnamed plant of *Neoregelia carolinae lineata*×*Neoregelia compacta*. The male or pollen parent was an unnamed plant of *Neoregelia fireball*, an unnamed species from Brazil known as *Neoregelia schultesiana* in Europe. 'Annick' was discovered and selected as a flowering plant within the progeny of the stated cross by Chester Skotak, Jr. in 1991 in a controlled environment in a nursery in Balsa, Costa Rica.

Subsequent asexual reproduction by removal of offsets has demonstrated that the combination of characteristics as herein disclosed for the new cultivar are firmly fixed and are retained through successive generations of asexual reproduction.

The new cultivar has not been observed under all possible environmental conditions. The phenotype may vary with variations in environment such as temperature, light intensity, and day length, without, however, any variation in the genotype of the plant. The following traits have been repeatedly observed and are determined to be basic characteristics of 'Annick' which in combination distinguish this Neoregelia as a new and distinct cultivar:

1. Leaves have a greyed-yellow margin (R.H.S 160B) and dark green center (R.H.S. 147A–B).

2. The innermost leaves at the center of the rosette, when in flower, are overlayed with red-purple (R.H.S. 59A–60A).

3. The innermost leaves at the center of the rosette hold their red-purple color for 3 to 5 months during and after flowering.

4. The plant produces large numbers of offsets.

The new variety Neoregelia 'Annick' can be compared to plants of the species *Neoregelia compacta*. 'Annick' has a well-developed rosette of leaves and is more compact than *Neoregelia compacta*. Neoregelia 'Annick' is also marginated (i.e., variegation on outer portion of leaf surface) whereas *Neoregelia compacta* is not marginated. *Neoregelia compacta* is almost spineless and Neoregelia 'Annick' has finely serrated margins.

In the photographic drawings, FIG. 1 comprises a side perspective view of a typical plant of the new cultivar.

Figure 2:
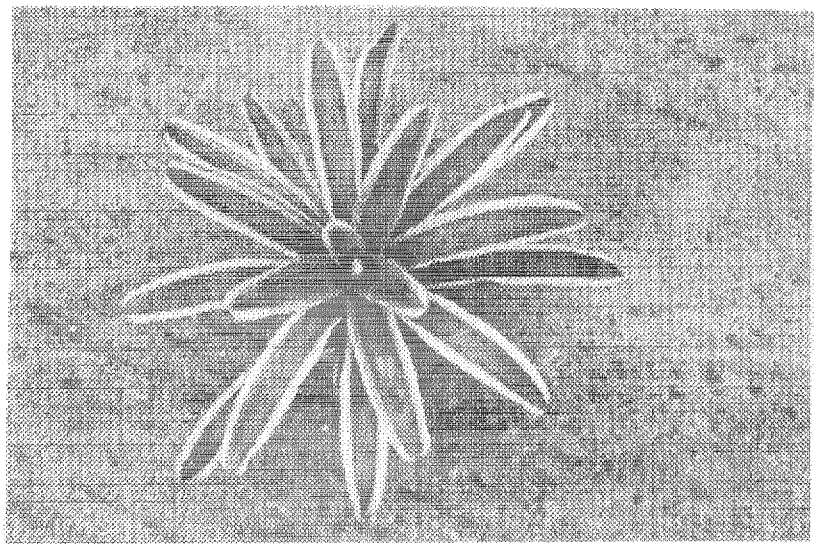

The photograph comprising FIG. 2 is a top view of the plant.

The following observations, measurements and values describe plants grown in Balsa, Costa Rica and Apopka, Fla., under greenhouse conditions which closely approximate those generally used in horticultural practice. Color references are made to The Royal Horticultural Society (R.H.S.) Colour Chart, except where general color terms of ordinary significance are used.

Classification:

*Botanical.*—Neoregelia hybrid, cv. 'Annick'.

*Commercial.*—Neoregelia 'Annick'.

Parentage:

*Male parent.*—Neoregelia 'Fireball'.

*Female parent.*—An unnamed plant of *Neoregelia carolinae lineata*×*Neoregelia compacta*.

Propagation:

Vegetative by removal of offsets.

Plant description:

*Form.*—From 20 to 24 cm tall when grown in 12.5 cm pots and approximately 40 cm or more in overall diameter when fully grown.

*Growth habit.*—Spreading rosette.

Leaves:

*Shape.*—Blades lingulate, recurved, broadly rounded and apiculate.

*Size.*—Length about 22–25 cm; width is 1 cm at tip and approximately 3.5 cm at middle.

*Margin.*—Finely serrated.

*Surface texture.*—Smooth.

*Veins or ribs.*—None.

*Color (R.H.S.)*:—Upper surface: Greyed-yellow margin (160B) and dark green center (147A–B), with slight variegation at the edges. The innermost leaves are overlayed with red-purple (59A–60A) and hold their color for approximately 3 to 5 months at the time of flowering.

*Lower surface.*—Smooth.

*Number of leaves.*—Average 25.

Rosette:

*Leaves forming the socket.*—The socket is about 2.5 cm in overall diameter.

*Color.*—Overlayed with red-purple 59A–60A, with the socket leaves holding their color for approximately 3 to 5 months at the time of flowering.

*Flowers.*—Arrangement: Inflorescence is deeply sunken rosette, simple and many flowered.

*Color.*—Petal apex violet-blue 91A with white base.

*Fruit.*—White, ovary slenderly ellipsoid and approximately 13 mm long.

*Duration of the flowers.*—Individual flowers last one day but flowering is continuous for 2 to 3 weeks.

Reproductive organs:

*Stamens.*—Pale yellow.

*Pistils.*—White; ovary is ellipsoid and approximately 13 mm long and 6 mm in diameter.

Disease resistance: Good resistance to fungi and insects exhibited in Costa Rica.

General observations: 'Annick' produces large numbers of offsets. Individual plants may produce up to 10 offsets per mature plant within a 3 to 10 month period.

I claim:

1. A new and distinct Neoregelia plant named 'Annick', as illustrated and described.

* * * * *